United States Patent [19]
Arbeit et al.

[11] Patent Number: 5,698,764
[45] Date of Patent: Dec. 16, 1997

[54] TRANSGENIC MICE EXPRESSING HPV EARLY REGION ONCOGENE DEVELOP PROGRESSIVE EPITHELIAL NEOPLASIA

[75] Inventors: Jeffrey M. Arbeit; Douglas Hanahan, both of San Francisco, Calif.; Peter M. Howley, Wellesley, Mass.

[73] Assignees: The Regents of the University of California, Rockville, Md.; The United States of America as represented by the Secretary of Health and Human Services, Washington, D.C.

[21] Appl. No.: 258,846

[22] Filed: Jun. 9, 1994

[51] Int. Cl.$^6$ .............................. C12N 5/00; C12N 15/00; A61K 49/00
[52] U.S. Cl. ..................... 800/2; 800/DIG. 1; 424/9.2
[58] Field of Search ......................... 800/2, DIG. 1; 435/320.1; 536/23.72, 24.1; 424/9, 9.2

[56] References Cited

PUBLICATIONS

Christofori, Gerhard, et al. (1994) "Molecular dissection of multi–stage tumorigenesis in transgenic mice", *seminars in Cancer Biology*, 5:3–12.

Arbeit, Jeffrey M., et al. (1993) "Neuroepithelial Carcinomas in Mice Transgenic with Human Papillomavirus Type 16 E6/E7 ORFs", *American Journal of Pathology*, 142(4):1187–1197.

Cheng, Jian, et al. (1992) "Cachexia and graft–vs.–host–disease–type skin changes in keratin promoter–driven TNFα transgenic mice", *Genes & Development*, 6:1444–1456.

Turksen, Kursad, et al. (1992) "Interleukin 6: Insights to its function in skin by overexpression in transgenic mice", *Proc. Natl. Acad. Sci. USA*, 89:5068–5072.

Vassar, Robert, et al. (1989) "Tissue–specific and differentiation–specific expression of a human K14 keratin gene in transgenic mice", *Proc. Natl. Acad. Sci. USA*, 86:1563–1567.

Arbeit, Jeffrey M., et al. (1994) "Progressive Squamous Epithelial Neoplasia in K14–Human Papillomavirus Type 16 Transgenic Mice", *Journal of Virology*, 68(7):4358–4368.

Munger et al. (1989) J. Virol. 63, 4417–4421.

Griep et al (1993) J. Virol. 67, 1373–1384.

Lambert et al (1993) Proced. Natl. Acad. Sci. 90, 5583–5587.

Del Vecchio et al (1992) J. Virol. 66, 5949–5958.

Guo et al (1993) EMBO J. 12, 973–986.

Masour et al (1988) Nature 336, 348–352.

Auborn, Karen, J., et al. (1991) "The Interaction Between HPV Infection and Estrogen Metabolism in Cervical Carcinogenesis", *Int. J. Cancer*, 49:867–869.

Münger, Karl, et al. (1992) "Interactions of HPV E6 and E7 Oncoproteins with Tumour Suppressor Gene Products", *Cancer Surveys*, 12:197–216.

Vassar, Robert, et al. (1991) "Transgenic mice provide new insights into the role of TGF–α during epidermal development and differentiation", *Genes & Development*, 5:714–727.

Kappel, et al. (1992) *Curr. Opin. in Biotech*, 3:548–553.

Shamay, et al. (1992) *Transgenic Res.*, 1:124–132.

Palmiter, et al. (1991) *PNAS*, 88:478–482.

*Primary Examiner*—Deborah Crouch
*Attorney, Agent, or Firm*—Townsend and Townsend and Crew, LLP

[57] ABSTRACT

The present invention relates to improved models for progressive epithelial neoplasias and methods for their use. In particular, the invention provides transgenic mice comprising a human papilloma virus early region oncogene operably linked to a promoter which directs expression of the oncogene in a transient amplifying cell in the mice.

12 Claims, No Drawings

TRANSGENIC MICE EXPRESSING HPV EARLY REGION ONCOGENE DEVELOP PROGRESSIVE EPITHELIAL NEOPLASIA

This invention was made with Government support under Grant No. 2R01CA47632-07A1 awarded by the National Institutes of Health. The Government has certain rights in this invention.

FIELD OF THE INVENTION

This invention pertains to the field of transgenic non-human animals. In particular this invention pertains to a Wansgenie animal that exhibits progressive epithelial neoplasia and methods of screening for therapeutics for progressive epithelial neoplasia.

BACKGROUND OF THE INVENTION

The most common malignancies in clinical practice arise in epithelia. An epithelium is the lining of a body surface that is exposed to the outside world, which places this tissue at risk for repeated damage from a variety of agents in the environment. Environmental carcinogens are the main suspects as major contributors to the development and spread of epithelial cancers. Examples of the most common epithelial cancers include lung, colon and breast carcinomas which are also the most prevalent cancers in industrialized countries. In the third world epithelial cancers such as liver and uterine cervical cancers account for the majority of cancer deaths. All of these cancers are associated with a diverse array of carcinogen exposures including cigarette smoke, estrogenic contaminants, toxic molds infecting grains, and infection with genital DNA tumor viruses.

A feature shared by most epithelial cancers is their multi-step progression to malignancy and are thus referred to as progressive epithelial neoplasias. The concept of multi-step carcinogenesis means that cancers do not appear "out of the blue", but evolve slowly over time during which the surrounding tissue becomes increasingly abnormal, and serves as fertile soil for the emergence of a full blown malignancy.

Closely related to the development of epithelial carcinomas is the progression of human papillomavirus (HPV) disease. HPV disease characteristically proceeds through multiple stages prior to the development of malignancy in a small number of patients. The initial hyperplastic phases of HPV disease are the proliferative lesions, which are called condyloma and genital warts. The normal morphology and differentiation of the cells in these lesions are maintained. Dysplastic lesions begin to appear in HPV lesions in which cellular morphology is altered and differentiation is perturbed. Dysplastic HPV lesions can further progress to invasive squamous cancers of either the uterine cervix or anus. The vast majority of infected individuals remain in the hyperplastic stage or revert to normal. A minority progress to dysplasia from which a smaller group inexorably advance to overt malignancy. Factors inherent in the host e.g., genetic susceptibility, nutritional deficiencies or environmental factors (e.g., multiple venereal infections or smoking) appear to coordinate continued progression to advanced stages of HPV neoplasia.

The extent of neoplastic progression is viral type specific; HPV6 and 11 cause condyloma acuminata which generally remain benign, while HPV16, 18, 33 and 35 are associated with intra-epithelial lesions that often progress to high grade lesions and occasionally to carcinomas (zur Hausen, *Cancer* 59:1692–1696 (1987)). While it is evident that HPV associated malignancy proceeds through multiple stages, the precise sequence of events and the factors determining the rate of progression to high grade dysplasia and invasive cancer have not been identified.

Thus the goals of both HPV research and epithelial carcinoma research are similar: to identify molecules that may coordinate progression from one stage to another, to understand the role these molecules play in the advancement of the neoplastic phenotype, and to identify therapeutics that treat early stages in the neoplastic progression to prevent progression and revert affected epithelium back towards normality.

Some of the most productive models of epithelial carcinogenesis have used the epidermis of the mouse, and have studied the response of murine skin to chemical carcinogens. In these systems either a single agent is repetitively administered, or a smaller dose of the agent is applied, followed by repetitive applications of a second agent that of itself cannot produce malignancy. These experimental paradigms are termed complete carcinogenesis, or initiation/ promotion respectively. These treatments last twenty weeks at which time the first papillomas appear and increase in number over time. Carcinomas develop in treated areas approximately 30–50 weeks after the start of treatment.

The difficulty with these chemical carcinogenesis studies are that a myriad of genetic alterations result from these treatments so that constructing a hierarchy of genetic change, whereby the functional significance of an alteration can be elucidated is extremely difficult. In addition, because the genetic changes associated with these treatment are unpredictable and multi-fold, animals expressing these carcinomas are highly variable and provide poor model systems for evaluating possible therapeutics.

Greater "uniformity" may be obtained by creating a transgenic animal that expresses carcinomas. Models of targeted expression of oncogenes to the epidermis of transgenic mice have been described. These models have used keratin promoters to target the expression of foreign DNA. Keratin are proteins that are expressed in epithelial tissues, and specific keratin proteins, identified by a number, e.g., keratin-5, are exclusively expressed not only in certain epithelia, but also in selected cells populating the epithelia. Initial transgenic models epidermal oncogene expression used keratin promoters suprabasal keratinocytes. The resulting phenotypes of these mice were early stage hyperplasias which did not progress further to either dysplasia or invasive cancers.

The basal cell specific keratin-14 (K14) promoter has been used to overexpress the growth factor TGF-$\alpha$ in the epidermis (Vassar et al. (1991) *Cell* 64: 365–380). These animals displayed a transient, neonatal hyperproliferation that disappeared in adults. Other workers have used promoters from genes specific to suprabasal cells to express growth factors, cytokines, and oncogenes in these cells (see, Cheng et al. (1992) *Genes Dev.* 6:1444–1456; Guo et aL (1993) *EMBO. J.* 12:973–986; Turksen (1992) *Proc. Natl. Acad. Sci. USA.* 89:5068–5072; and Vassar et al. (1989) *Proc. Natl. Acad. Sci. USA* 86:1563–1567). Recently, a report appeared describing the expression of the principle oncogenes of HPV 16, e.g., the E6 and E7 open reading frames, under control of a lens $\alpha$-crystalline promoter (Lambert et al. (1993) *Proc. Natl. Acad. Sci. USA* 90:5583–5587). These transgenic mice serendipitously express the HPV 16 oncogenes in their epidermis, and only 20% of hyperplastic lesions progress to invasive squamous cancers. The neoplastic stages of these animals has not been

3 well characterized, at least in the literature, so that the quality of multi-step carcinogenesis in this system is difficult to assess. Thus, these animals do not provide a reliable and reproducible model for the study of progressive epithelial neoplasia.

Similarly, there is no transgenic model of cervico-vaginal neoplastic progression. There have been efforts to directly infect the cervix and vaginal mucosa of mice with retroviral vectors containing HPV16 oncogenes. These experiments are cumbersome requireing the platmerit of cotton tampons soaked with retroviral vectors. Mice treated in this manner develop hyperplastic lesionf of the cervico-vaginal mucosa, but the lesions do not apear to advance to higher grades of dysplasia.

Despite some progress good models for the study of many carcinomas are still needed. For instance, models specific to a specific carcinoma such as cervical carcinomas would be particularly useful. The present invention addresses these and other needs.

SUMMARY OF THE INVENTION

The present invention provides transgenic non-human animals exhibiting progressive epithelial neoplasia caused by a human papilloma virus oncogene operably linked to a promoter which directs expression of the oncogene in a transient amplifying cell, typically a basal keratinocyte, in the non-human animal, preferably a mouse. The oncogene can be from any human papilloma virus, preferably papilloma virus 16. The oncogene can be incorporated as part of the early region of an human papilloma virus genome. The promoter used to drive expression of the oncogene is preferably a keratin-14 promoter.

The animal may further comprise a β-galactosidase gene operably linked to a promoter which directs expression of the β-galactosidase gene in a transient amplifying cell. If the oncogene is expressed in a basal keratinocyte, the β-galactosidase gene is also preferably expressed in a basal keratinocyte.

The invention also provides recombinant DNA constructs comprising an expression cassette including a human papilloma virus oncogene operably linked to a promoter which directs expression of the oncogene in a transient amplifying cell, such as a basal keratinocyte. The promoter is preferably the keratinocyte-14 promoter.

The invention further provides methods of testing a composition for the ability to inhibit epithelial neoplasia induced by a human papilloma virus oncogene. The methods comprise providing a transgenic non-human animal comprising a human papilloma virus oncogene operably linked to a promoter which directs expression of the oncogene in a transient amplifying cell, administering the composition to the non-human animal, and detecting epithelial neoplasia in the non-human animal.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The "non-human animals" of the invention comprise any non-human animal or mammal having an tissues in which cells express and utilize mdr1-type gene products. Such non-human animals include vertebrates such as non-human primates, ovine, canine, bovine, ratms and murine species as well as rabbit and the like. Preferred non-human animals are selected from the rodent family including rat, guinea pig and mouse, most preferably mouse.

The phrase "progressive epithelial neoplasia" refers to a multi-step progression to malignancy. The concept of multi-step carcinogenesis means that cancers evolves slowly over time during which the surrounding tissue becomes increasingly abnormal. The features of the early, intermediate and advanced stages of multi-step malignant progression have been described using microscopy. The first stage of neoplastic progression is an increased number of relatively normal appearing cells, the hyperplastic stage. There are several stages of hyperplasia in which the epithelial cells progressively accumulate and begin to develop an abnormal appearance, which is the emergence of the dysplastic phase. Dysplastic cells resemble immature epithelial cells, and during this phase of epithelial neoplastic progression, an increasing percentage of the epithelium is composed of these immature cells. Eventually, invasive cancers develop in epithelia severely affected by dysplasia.

The term "transient amplifying cells" refers to proliferating epithelial cells. There are two types of proliferating cells in epithelia, stem cells and transient amplifying cells (Cotsarelis et al. (1990) *Cell* 61: 1329–1337). The former, which divide slowly but perpetually, are located in the bulge region of the hair follicle or in the deep rete ridges (Id.), while the latter, which rapidly proliferate for a limited time prior to terminal differentiation, are the basal cells distributed both in the interfollicular regions and outer root sheaths (Id.). Transient amplifying cells are the presumed targets for neoplastic conversion in epithelia that are exposed to the environmental carcinogens, e.g., murine chemical carcinogenesis models and human colon cancers. This susceptibility may be related to their rapid cell cycles, which may not allow effective repair of DNA damage (Id.). Transient amplifying cells include squamous epithelial basal cells and their counterparts in other epithelia such as intestine, lung, breast and the like.

"Operably linked" when describing the relationship between two polynucleotide sequences, means that they are functionally related to each other. For example, a promoter is operably linked to a coding sequence if it controls the transcription of the sequence; a ribosome binding site is operably linked to a coding sequence if it is positioned so as to permit translation, etc.

The term "early region of a human papilloma virus genome" refers to that portion of the genome comprising HPV oncogenes. The gene products of the HPV early region have been well characterized. The principle transforming genes of the cancer associated HPV's are E6 and E7. The remainder of the early region encodes the E2 transactivator/repressor, the E1 protein, the E4 protein, and the E5 protein. Progression of HPV disease is associated with changes in the state of the viral genome and in patterns of viral transcription that may contribute to the development of malignancy.

The term "oncogene" refers to a gene that causes the synthesis of new proteins in a cell that alter the control of cellular proliferation. Such genes may be of either cellular or viral origin. The present invention focusses primarily on oncogenes derived from human papilloma virus.

An "estrogen-like compound" of the invention is a naturally occurring estrogen, as well as a synthetic analog which is typically a related steroid compound capable of binding an estrogen receptor in uterine tissue and inducing a agonistic response. Naturally occurring estrogens include 17β-estradial and estrone, and estriol.

DETAILED DESCRWTION

The present invention relies in part on the discovery that a transgenic animal containing expression cassettes containing human papillomavirus (HPV) oncogenes targeted for expression in transient amplifying cells displays progressive epithelial neoplasias that serve as useful models for the development of a number of carcinomas.

The oncogene products of the HPV early region have been well characterized. The principle transforming genes of the cancer associated HPV's are E6 and E7 (Münger, et al. (1992) *Cancer Surveys* 12: 197–217). The E6 oncoprotein targets the proteolysis of p53 through the ubiquitination pathway (Scheffner et al. (1990) *Cell* 63:1129–1136), whereas the E7 protein binds the retinoblastoma protein (Dyson et al. (1989) *Science*, 243: 934–937) and related proteins p107 and p130 (Dyson et al. (1992) *J. Virol.* 66: 6893–6902), and in so doing releases E2F, a transcription factor, which transactivates several proliferation associated genes (Chellappan et al. (1992) *Proc. Natl. Acad. Sci. USA*, 89: 4549–4553). The remainder of the early region encodes the E2 transactivator/repressor, the E1 protein which binds to the origin of replication, the E4 protein, which has been shown to dissociate actin intermediate filaments, and the E5 protein, which increases the activity of both the EGF or PDGF receptors (Howley, (1989) *Papillomaviruses and Their Replication*, p. 1625–1650. In Fields et al. (ed.) *Virology*, 2nd Edition. Raven Press, New York).

Progression of HPV disease is associated with changes in the state of the viral genome and in patterns of viral transcription that may contribute to the development of malignancy. In condylomas, papillomas and mild/moderate dysplasias, the virus is episomal (Crum et al. (1984) *New Engl. J. Med.*, 310: 880–883; Cullen et al. (1991) *J. Virol.* 65: 606–612), and the entire early region is expressed (Shirasawa et al. (1988) *J. Virol.* 62: 1022–1027). In high grade dysplasias and in cancers, the vital DNA is integrated into the host genome. Integration frequently occurs in the E1/E2ORF, disrupting the early region downstream of the E7 coding region, and potentially leading to deregulated expression of the E6 and E7 ontoproteins, due to the absence of E2 transcriptional regulation (Baker et al. (1987) *J. Virol.* 61: 962–971; Schwarz et al. (1985) *Nature*, 314: 111–114; Smotkin, et al. (1986) *Proc. Natl. Acad. Sci. USA.* 83: 4680–4684). These changes in viral structure and expression patterns during clinical progression suggest that the functions of the viral early region are necessary to initiate cellular proliferative and dysplastic changes, whereas the E6 and E7 oncoproteins may be sufficient to maintain high grade dysplasia and malignancy.

Evidence provided here demonstrates that transgenic non-human animals which express these genes in transient amplifying cells and exhibit progressive epithelial neoplasia which serves as useful model for HPV-induced neoplastic progression. These mice can be used test the efficacy of new anti-neoplastic agents administered alone or in combination with carcinogens. In addition, the animals can be used for models of specific carcinomas by administering to the animals compounds known to induce certain carcinomas. As demonstrated below, administration of estrogens to transgenic mice lead to the development of cervical carcinoma.

Generally, the nomenclature used hereafter and the laboratory procedures in molecular genetics described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. Much of the nomenclature and general laboratory procedures described below can be found in Sambrook, et al., *Molecular Cloning - A Laboratory Manual* (2nd Ed.), Vol. 1–3, Cold Spring Harbor Laboratory, Cold Spring Harbor, New York, 1989.

I. Vector construction

Appropriate constructs and methods for production of transgenic animals, particularly mice, are described, for instance, in Hogan et al. *Manipulating the Mouse Embryo*, Cold Spring Harbor Laboratory, Cold Spring Harbor, N.Y. (1986). In the construction of vectors for the production of transgenic animals, the coding sequence of interest is typically operably linked to expression regulatory sequences. In such transgenes, the expression regulatory sequence is at least the minimal sequences required for efficient cell-type specific expression, which generally are at least a promoter and at least about 1 kilobase (kb) upstream of the promoter. Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a transgene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a transgene.

Typically, expression regulation sequences are chosen to produce tissue-specific or cell type-specific expression of the desired structural gene. In the present invention the targeted cells are transient amplifying cells. Once a tissue or cell type is chosen for expression, expression regulation sequences are chosen. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal.

The constructs will usually also comprise downstream expression regulation sequences to supplement tissue or cell-type specific expression. The downstream expression regulation sequences include polyadenylation sequences (either from the endogenous gene or from other sources such as SV40) and sequences that may affect RNA stability as well as enhancer and/or other sequences which enhance expression.

In the present invention, an HPV16 DNA sequence is placed in an expression cassette under the control of a promoter that will direct expression to transient amplifying cells. A number of suitable promoters can be used for this purpose. The particular promoter is not critical to the invention, so long as it directs expression to transient amplifying cells. Particularly useful for targeting the expression of HPV DNA sequences to transient amplifying cells are the promoters from genes encoding keratin. Keratin are proteins that are expressed in epithelial tissues, and specific keratin proteins, identified by a number e.g., keratin-5 are exclusively expressed not only in certain epithelia, but also in selected cells populating the epithelia. The epidermis is composed of layers of cells (keratinocytes) which produce specific types of kentin proteins. The basal cells produce kentin 5 and 14 (K5 and K14), whereas the more mature, terminally differentiated keratinocytes, e.g., the suprabasal keratinocytes, produce K10 and K1. Promoters from other keratin genes, such as K8 and K19 are useful in direct expression to epithelia in the bladder or intestines. In a preferred embodiment a basal cell keratin promoter (e.g., K5 or K14) is utilized and the K14 promoter is particularly preferred.

A K14 expression cassette, containing 2 kb of the K14 promoter/enhancer and 500 bp of 3' flanking sequence including the K14 polyadenylation signal, has been shown to appropriately target expression of transgenes to the basal cells of squamous epithelium (Vassar et al. (1991) *Cell*, 64: 365–380; Cheng et al. (1992) *Genes Dev.* 6: 1444–1456; Guo et al. (1993) *EMBO. J.*, 12: 973–986; Turksen et al. (1992) *Proc. Natl. Acad. Sci. USA*. 89: 5068–5072; and Vassar et al. (1989) *Proc. Natl. Acad. Sci. USA*, 86: 1563–1567). This cassette is particularly suitable for construction of the K14-HPV transgene of the present invention.

In preferred embodiments, the HPV16 early region is used in the expression cassettes of the invention. The entire early region in contrast to the E6 and E7ORFs alone is preferred because it may coordinate the early stages of clinical HPV16 disease. Moreover, when placed under control of a heterologous promoter, it is more potent than the E6/E7 oncogenes alone in keratinocyte immortalization assays. One of skill in the art will recognize that a number of versions of the HPV16 early region are suitable. Variations may be derived from plasmids p1203, p16Nt, and p16Pt described by Del Vecchio et al. (1992) *J. Virol.*, 66: 5949–5958. Methods of modifying these and other plasmids containing HPV gene sequences are well known to those of skill in the art (see, for example, Sambrook et al., (1989) supra, *Methods in Enzymology* (1987) Vol. 152: *Guide to Molecular Cloning Techniques* (Berger and Kimmel (eds.), San Diego: Academic Press, Inc., or Ausubel et al. (1987) *Current Protocols in Molecular Biology*, Greene Publishing and Wiley-Interscience, N.Y.).

I. Production of Transgenic Animals

The transgenic non-human animals of the invention are produced by introducing expression cassettes comprising the HPV oncogenes into the germline of the non-human animal. In preferred embodiments two expression cassettes are introduced into the animal. One cassette comprises the HPV oncogenes and the other comprises selectable marker gene such as β-galactosidase or β-glucuronidase (GUS). Genes encoding β-galactosidase are particularly preferred. Embryonic target cells at various developmental stages can be used to introduce transgenes. Different methods are used depending on the stage of development of the embryonic target cell.

A. MicroInjection Methods

Microinjection is a preferred method for transforming a zygote or early stage embryo. In the mouse, the male pronucleus reaches the size of approximately 20 micrometers in diameter which allows reproducible injection of 1–2pl of DNA solution. The use of zygotes as a target for gene Wansfer has a major advantage in that in most cases the injected DNA will be incorporated into the host gene before the first cleavage (Brinster, et al. (1985) *Proc. Natl. Acad. Sci. USA* 82: 4438–4442). As a consequence, all cells of the transgenic non-human animal will carry the incorporated transgene. This will, in general, also be reflected in the efficient transmission of the transgene to offspring of the founder since 50% of the germ cells will harbor the transgene.

The gene sequence being introduced need not be incorporated into a self-replicating plasmid or virus (Jaenisch, (1988) *Science*, 240:1468–1474 (1988)). However, in a preferred embodiment, the gene sequence will be introduced in a as a cassette comprising the gene under the control of a promoter. The promoter acts to regulate transcription of the gene in response to endogenous factors present in a particular tissue and thus results in tissue-specific expression of the gene.

Once the DNA molecule has been injected into the fertilized egg cell, the cell is implanted into the uterus of a recipient female, and allowed to develop into an animal. Since all of the animal's cells are derived from the implanted fertilized egg, all of the cells of the resulting animal (including the germ line cells) shall contain the introduced gene sequence. If, as occurs in about 30% of events, the first cellular division occurs before the introduced gene sequence has integrated into the cell's genome, the resulting animal will be a chimeric animal.

By breeding and inbreeding such animals, it has been possible to produce heterozygous and homozygous transgenic animals. Despite any unpredictability in the formation of such transgenic animals, the animals have generally been found to be stable, and to be capable of producing offspring which retain and express the introduced gene sequence.

The success rate for producing transgenic animals is greatest in mice. Approximately 25% of fertilized mouse eggs into which DNA has been injected, and which have been implanted in a female, will become transgenic mice. A number of other transgenic animals have also been produced. These include rabbits, sheep, cattle, and pigs (Jaenisch (1988) *Science* 240: 1468–1474; Hammer et al., (1986) *J. Animal Sci*, 63:269; Hammer et al. (1985) *Nature* 315: 680; Wagner et al., (1984) *Theriogenology* 21: 29).

B. Retroviral Methods

Retroviral infection can also be used to introduce a transgene into a non-human animal. The developing non-human embryo can be cultured in vitro to the blastocyst stage. During this time, the blastomeres can be targets for retrovital infection (Jaenich (1976) *Proc. Natl. Acad. Sci USA* 73: 1260–1264). Efficient infection of the blastomeres is obtained by enzymatic treatment to remove the zona pellucida (Hogan, et al. (1986) In *Manipulating the Mouse Embryo*, Cold Spring Harbor Laboratory Press, Cold Spring Harbor, N.Y.). The viral vector system used to introduce the transgene is typically a replication-defective retrovirus carrying the transgene (Jahner, et al. (1985) *Proc. Natl. Acad. Sci. USA* 82, 6927–6931; Van der Putten, et al. (1985) *Proc. Natl. Acad. Sci. USA* 82, 6148–6152). Transfection is easily and efficiently obtained by culturing the blastomeres on a monolayer of virus-producing cells (Van der Putten, supra; Stewart et al. (1987) *EMBO J.*, 6: 383–388). Alternatively, infection can be performed at a later stage. Virus or virus-producing cells can be injected into the blastocoele (Jahner et al. (1982) *Nature*, 298: 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner et al. (1982) supra).

C. ES Cell Implanation

A third target cell for transgene introduction is the embryonic stem cell (ES). ES cells are obtained from pre-implantation embryos cultured in vitro (Evans et al. (1981) *Nature*, 292: 154–156; Bradley, et al. (1984) *Nature*, 309: 255–258; Gossler, et al. (1986) *Proc. Natl. Acad. Sci USA* 83:, 9065–9069; and Robertson, et al. (1986) *Nature*, 322: 445–448). Transgenes can be efficiently introduced into ES cells using a number of means well known to those of skill in the art. Such transformed ES cells can thereafter be combined with blastocysts from a non-human animal. The ES cells thereafter colonize the embryo and contribute to the germ line of the resulting chimeric animal (for a review see Jaenisch (1988) *Science*, 240: 1468–1474).

In a preferred embodiment, the DNA is introduced by electroporation (Toneguzzo et al., (1988) *Nucleic Acids Res.*, 16: 5515–5532; Quillet et al. (1988) *J. Immunol.*, 141: 17–20; Machy et al. (1988) *Proc. Nat'l. Acad. Sci. USA*, 85: 8027–8031). 8031). After permitting the introduction of the DNA molecule(s), the cells are cultured under conventional conditions, as are known in the art.

In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable (selectable) marker gene sequence. The presence of the detectable (selectable) marker sequence in a recipient cell may be recognized by PCR, by detection of radiolabelled nucleotides, or by other assays of detection which do not require the expression of the detectable marker sequence. Typically, the detectable marker gene sequence will be expressed in the recipient cell, and will result in a selectable phenotype. Selectable markers are well known to those of skill in the art. Some examples include the hprt gene (Littlefield (1964) *Science* 145: 709–710), the tk (thymidine kinase) gene of herpes simplex virus (Giphart-Gassler et al. (1989) *Mutat, Res.*, 214: 223–232), the nDtII gene (Thomas et al. (1987) *Cell,* 51: 503–512; Mansour et al. (1988) *Nature* 336: 348–352), or other genes which confer resistance to amino acid or nueleoside analogues, or antibiotics, etc.

Any ES cell may be used in accordance with the present invention. It is, however, preferred to use primary isolates of ES cells. Such isolates may be obtained directly from embryos such as the CCE cell line disclosed by Robertson, E. J., In: *Current Communications in Molecular Biology*, Capecchi, M. R. (ed.), Cold Spring Harbor Press, Cold Spring Harbor, N.Y. (1989), pp. 39–44), or from the clonal isolation of ES cells from the CCE cell line (Schwartzberg et al. (1989) *Science* 212: 799–803). Such clonal isolation may be accomplished according to the method of Robertson (1987) In: *Teratocarcinomas and Embryonic Stem Cells: A Practical Approach,* E. J. Robertson, Ed., IRL Press, Oxford. The purpose of such clonal propagation is to obtain ES cells which have a greater efficiency for differentiating into an animal. Clonally selected ES cells are approximately 10-fold more effective in producing transgenic animals than the progenitor cell line CCE.

II. Verification of the presence of the transgene in the animal

A number of methods used to detect particular polynucleotide sequences can be used to verify that the desired sequences have been integrated into the genome of the transgenic animal. For instance, Fluorescent In Situ Hybridization (FISH) can be used to detect the transgene in tissue from the animal. Several guides to FISH techniques are available, e.g., Gall et al. *Meth. Enzymol.*, 21:470–480 (1981) and Angerer et al. in *Genetic Engineering: Principles and Methods* Setlow and Hollaender, Eds. Vol 7, pgs 43–65 (plenum Press, New York 1985). Alternatively, DNA or RNA can be isolated for tissue (typically tail tissue). The desired sequences can be detected by Southern or Northern hybridization or by PCR using primers and probes specific for the transgene. Standard PCR methods useful in the present invention are described in PCR *Protocols: A Guide to Methods and Applications* (Innis et al., eds., Academic Press, San Diego 1990).

Alternatively, expression of the integrated gene can also be detected by detecting the gene product. The protein can be detected, for instance, using standard immunoblotting techniques, well known to those of skill in the art.

III. Assays Utilizing the Transgenic Animals of the Present Invention

Unique features of the transgenic animals of the present invention include the multiplicity of squamous epithelial sites affected by expression of the transgene, and the discrete multi-step neoplastic progression of the epidermis. The former aspect of this model can be utilized to assess the systemic co-carcinogenicity of multiple environmental agents, and conversely the ability of chemopreventives to abrogate this systemic initiation. The multi-step epidermal progression, is a dose facsimile of both clinical HPV disease in particular and epithelial carcinogenesis in general, and thus can be utilized to investigate topical co-carcinogenesis and/or chemoprevention, as they interact with a cancer associated DNA tumor virus. Since the transgenic mice of the invention develop a neoplastic progression that closely resembles human carcinogenesis, they are powerful models for developing novel therapeutics.

One of skill would recognize that there are a number of approaches to the use of these transgenic animals for the design and screening of antineoplastic drugs. One approach involves using the animals as screening systems to identify and characterize the molecules that coordinate the onset and development of hyperplasia and dysplasia, as well as the molecules that regulate the infrequent, spontaneous malignant conversion of a fraction of these lesions. Characterization of these molecules could lead to the design of novel drugs that would specifically inhibit candidates that are over-expressed or replace the function of regulatory molecules that are lost during neoplastic progression.

Another approach involves the screening and identification of potential carcinogens directly. This involves exposing the transgenic animal to different agents and determining whether the neoplastic progression of the transgenic animal is accelerated, inhibited, or altered in quality. These experiments model the epidemiological scenario of exposure of entire populations to environmental carcinogens and the response of individuals that may be harboring a variety of genetic alterations, either inherited, or acquired in the form of a DNA tumor virus, that would make these individuals more susceptible to environmental mutagens. The transgenic animals of this invention provide an excellent model with which to study these interactions because: 1) the multiple affected squamous epithelial sites enable study of mucosal neoplastic progression in response to a systemic carcinogen, a situation similar to the increased incidence of a variety of extrapulmonary epithelial cancers in smokers; and 2) the neoplastic progression in the skin which facilitates the study of direct toxicity of environmental carcinogens on an exposed epithelium.

Other applications of this model would be to test the efficacy of novel antineoplastic drugs administered alone or concomitantly with carcinogens to investigate their ability to prevent neoplastic disease. Examples of some existing chemopreventive agents include the vitamin A derivatives, e.g., the retinoids, and the vitamin D analogs. Since the major affected area of the mice of the invention is the skin, these chemopreventive drugs could be topically applied or systemically administered. In addition since the skin can be visually inspected, the efficacy of these agents can be immediately and continually assessed.

One of skill would immediately recognize how to conduct such assays utilizing the transgenic non-human animals of the present invention. In general such assays simply involve administering the potential carcinogen, therapeutic, or combination of carcinogen and therapeutic to the transgenic animal and then detect the existence or progression of epithelial neoplasia in the animal. Neoplasias can be detected according to standard techniques well known to those of skill in the art. Such methods include visual inspection (for lesions on the skin), immunohistochemical techniques, and the like.

One of skill would recognize that numerous modes of administration are possible. Modes of administration include, but are not limited to, topical application, intra- and subdermal injection, aerosol administration, and transdermal administration (e.g. in a carrier such as DMSO). Of course the selection of a particular mode of administration will reflect the particuladties of the composition. Thus, for example, where carcinogens are screened they will be applied in a manner that reflects their occurrence in the environment. Similarly where a potential therapeutic is expected to be administered topically as opposed to systemically, the potential therapeutic will be screened using a topical application.

IV. Administration of the Transgenic Non-Human Animals With Estrogen-like Compounds Produces a Useful Model of Cervico-Vaginal Neoplastic progression The treatment of the transgenic animals of this invention with exogenous estrogen or estrogen-like compounds turns on transgene expression in the squamous mucosal basal cells of both the vagina and the cervix. Further, of greater clinical and therapeutic relevance, is that estrogen induced HPV16 transgene expression produces a neoplastic progression that faithfully resembles the gynecological dysplastic lesions induced by high risk HPV'S. In particular, estrogen treatment conditionally and selectively upregulates the expression of HPV16 not only in the clinically relevant target tissue; the gynecological squamous epithelium, but also within the critical cells, the basal keratinocytes, within this epithelium. Estrogen treatment is therefore able to induce the precise pathology, cervico-vaginal squamous dysplasia that is caused by HPV16 disease in humans. Thus, the estrogen-treated transgenic animals of the present invention provide a good model of cervico-vaginal neoplastic progression.

One of skill in the an would recognize that there are a large number of uses of the this model of gynecological malignancy. One use is to investigate the effect of prolonged exposure to estrogen or related compounds. A second use is to provide additional genetic alterations by mating two different K14 transgenic mice to generate double transgenic mice expressing two oncogenes both regulated by the K14 promoter, and then to assay for the effect of estrogen treatment of these double transgenic mice accelerates the neoplastic phenotype. A third use is the use of this model of sex-hormone induced neoplastic progression as a screening system to investigate the effect of estrogen and estrogen-like compounds as well as their antagonists on the cervico-vaginal neoplastic progression. Of course, the model is also useful for screening potential therapeutic drugs and chemopreventive agents that would prevent the development of dysplasia or cancers.

In the case of mice, intermediate duration treatment with estrogen induces mild to moderate cervico-vaginal dysplasia over 2–4 months. Given that the epidermis of the transgenic mice requires 8–12 months in order to develop invasive squamous cancers in areas of high grade dysplasia, a similar duration of estrogen treatment of transgenic mice (6–12 months), is required to set the stage for earcinoma induction in the cervix and vagina. Furthermore spontaneous malignant conversion of epidermal dysplasias is infrequent in the transgenic mice, secondary to a requirement for the recruitment of additional cellular events which contribute to the formation of carcinomas. 17-β-estradiol itself can be converted to free radicals in estrogen responsive tissues. These free radicals damage DNA and provide the source for additional cellular mutations which contribute to malignancy. Thus prolonged estrogen treatment provides a dual route to malignant progression; an alternation of the cellular context which facilitates HPV 16 induced dysplasia, and additional cellular genetic mutations which advance HPV 16 neoplastic progression towards malignancy.

A way to provide specific, discrete additional genetic alterations that are selectively expressed in cervico-vaginal mucosa is to generate double transgenic mice carrying both an HPV transgene and the candidate mutant gene, both under control of a keratin promoter. During estrogen treatment both of these transgenes are selectively upregulated specifically in the cervico-vaginal squamous mucosa. Thus the approach of estrogen treatment of transgenic mice carrying keratin promoter regulated transgenes presents a powerful general method to model synergism between selected candidate genetic mutations in squamous mucosa of the female reproductive tract.

Finally the transgenic animals of this invention treated with estrogen, estrogen-like compounds, and estrogen agonists and antagonists (e.g. tamoxifen and megesterol) alone or in combination provides a good model system in which to screen drags and treatments designed to prevent HPV induced cervico-vaginal neoplastic progression. One group of candidate drugs are the retinoids which have already been tested in clinical trials in patients with HPV disease. There is intensive research directed towards the chemoprevention of HPV induced neoplastic progression through the development of more efficacious and specific retinoid compounds. Further research into the mechanisms of estrogen induced HPV neoplastic progression using the transgenic mice of the invention could provide sufficient data for the design of novel and potent retinoid compounds. The other group of candidate drugs which would be relevant for testing in our model are the anti-estrogens and the antiproliferative synthetic progestins. These agents are continuously being developed for treatment of gynecological and breast malignancies, and their ability to circumvent a genetically programmed cevico-vaginal neoplastic progression could also be tested in this model. Thus the estrogen treated transgenic animals may form a cornerstone for field testing of novel agents directed against hormonally induced cancers by the pharmaceutical industry.

One of skill in the art would recognize that assays of this sort involve administering estrogen or an estrogen-like compound, alone or in combination with another agent (e.g. 16 methoxyestradiol, 17α-estrogen, tamoxifen, progesterone, megesterol, etc.), and detecting the progression of cervico-vaginal dysplasia. Combinations of such compounds are of particular interest. For example, estrogen and progesterone are common constituents of oral contraceptives and the transgenic animal treated with this combination provides a good model system for the investigation of the effect of oral contraceptives, alone or in combination with other agents, on the progression of cervico-vaginal dysplasia. Similarly, tamoxifen, which is used as an anti-estrogen in the treatement of breast cancer, shows agonist behaviour in uterine tissue. A combination of estrogen and tamoxifen provides a good model organism for screening the effect of various agents in this context. The use of the compound 16-methoxy estradiol acts as an inhibitor of angiogenesis and thus, when applied to the transgenic animals of this invention, provides a system useful for investigating the effect of agents on the progression of dysplasia where circulatory proliferation is limited. The foregoing discription is simply illustrative of a few possibilities, numerous other assays will be recognized by those of skill in the art.

The mode of application of such agents and detection of the progression of cervico-vaginal dysplasia will depende on the particular circumstances as described above.

EXAMPLES

A) Materials and Methods

The Examples described herein utilize the following materials and methods.

1. Histology

Tissues were immersion fixed overnight at 4° C. in fresh 3.75% paraformaldehyde in calcium/magnesium free phosphate buffered saline. They were processed through graded alcohols, 3 changes of xylene and embedded in paraffin. Sections (5 µm) were stained with hematoxylin/eosin.

2. 5-Bromo-2'-deoxyuridine (BrdU) Incorporation

Animals were injected intraperitoneally with 100 µg/g body weight of a 5 mg/ml solution of BrdU (Sigma, St Louis, Mo., USA) in a 10 mM Tris/0.9% saline/1 mM EDTA pH 8.0 buffer. After 2 hours the animals were sacrificed, and tissues were fixed, processed, embedded in paraffin, and 5 µm sections were obtained. After deparaffinization, and rehydration, the slides were immersed in 2N HCl for 1 hr, extensively rinsed in tap water, and equilibrated in PBS. The sections were then treated for 60 sec with 0.1% bacterial protease, (Sigma Type XXIV, St Louis, Mo., USA), rinsed extensively in tap water, equilibrated in PBS, and blocked in 3 % normal goat serum. A 1:50 dilution of a biotinylated mouse monoclonal anti-BrdU antibody (Cal-Tag, Br-3, Burlingame, Calif., USA) was applied, and the sections incubated overnight at 4° C. Antibody binding was detected using a peroxidase/avidin/biotin complex (ABC, Vector Elite, Burlingame, Calif., USA), with 3,3'-diaminobenzidine (Sigma, St Louis, Mo.) as the chromogen.

3. Immunohistochemistry

Paraffin sections (5 µm) were stained with the following types and titers of specific antisera or affinity purified antibodies: rabbit anti-human K14, 1:1000, rabbit anti-human K5, 1:1000, affinity purified rabbit anti-mouse K10, 1:1000 and rabbit anti-mouse filaggrin, 1:1000. A 1:200 dilution of a peroxidase conjugated goat anti-rabbit antibody was used as the secondary antibody (Vector, Burlingame, Calif., USA), and specific binding was detected using the reagents described in the previous section.

4. Southern Blotting

DNA (5 µg) was digested with EcoRV, electrophoresed through 0.6% agarose gels, and transferred to nylon (Magnagraph, MSI, Westborough, Mass.). Prehydridization and hybridization were performed according to the manufacturers instructions. The probe was a 800 bp fragment encompassing the E6/E7ORF's. Plasmid reconstructions corresponding to 1, 5, 10 and 25 copies were run concurrently to determine copy number (Arbeit, et al., *Am. J. Path.* 142:1187–1197 (1993)).

5. RNA-PCR

RNA was isolated from pieces of tail clipping (100 mg) using a variation of the acid-phenol-guanidinium technique (Chomcyznski, et al., *Anal Biochem* 162:156–159 (1987)). Total RNA (1 µg) was reverse transcribed and the cDNA was amplified using primers the spanned the E6ORF to encompass the E6* splice site (Arbeit, et al., *Am. J. Path.* 142:1187–1197 (1993)). PCR products were visualized by ethidium bromide staining of 2.0% agarose gels. The identity of the reaction products with HPV16 sequences have been previously confirmed by Southern blotting (Arbeit, et al., *Am. J. Path.* 142:1187–1197 (1993)).

6. HPV16 E7 protein expression

HPV16 E7 protein was detected using a combined immunoprecipitation/Western blotting technique previously described (Arbeit, et al., *Am. J. Path.* 142:1187–1197 (1993)). Two-day old mice were sacrificed and the entire full thickness skin extending from the hind limbs to fore limbs was circumferentially removed from the torso, cleaned of adipose tissue, and snap frozen in liquid nitrogen. The samples were pulverized over solid $CO_2$, and the powder was rapidly homogenized in a RIPA buffer containing protease inhibitors (Arbeit, et al., *Am. J. Path.* 142:1187–1197 (1993)). After pre-clearing at 15000 X g, the total protein content was determined in the supernatant (Bio Rad, Richmond, Calif., USA), and a volume corresponding to 500 µg of total protein was cleared with protein A sepharose/rabbit IgG, and used for immunoprecipitation with a rabbit polyclonal E7 antibody. After electrophoresis and Western transfer to a PVDF membrane (Immobilon, Millipore, Bedford, Mass., USA), a monoclonal E7 antibody (Triton, Alameda, Calif., USA) was used for detection, and the signal was developed using the ECL system (Amersham, Arlington Hts, Ill., USA).

Example 1

Creation of Transgenic Mice

The K14 expression cassette contains 2 kb of the K14 promoter/enhancer and 500 bp of 3' flanking sequence including the K14 polyadenylation signal. This construct has been shown to appropriately target expression of transgenes to the basal cells of squamous epithelium (Vassar, et al., *Genes Dev.* 5:714–727 (1991)). There were three variations of the HPV16 early region used this study, derived from plasmids p1203, p16Nt and p16Pt (Del Vecchio, et al., *J. Virol.* 66:5949–5958 (1992)). Plasmid p1203 contained wild type HPV16 genome. Plasmid p16Nt was derived from p1203, but contained a translation termination linker (TTL) in the E1ORF at nucleotide 1311. Plasmid p16Pt contained a TrL in the E2ORF at nucleotide 2922. Fragments encompassing the entire HPV16 early coding region from bp 97 to bp 6152, were excised from these plasmids and cloned into the BamHI site of the K14 expression plasmid to generate the plasmids pK14-1203, pK14-16Nt and pK14-16Pt as previously described (Del Vecchio, et al., *J. Virol.* 66:5949–5958 (1992)). For the sake of simplicity, these plasmids will be referred to as K14-wt, K14-E1$_m$ and K14-E2$_m$ respectively. The immortalization efficiency of these constructs for human keratinocytes was K14-E2$_m$>K14-E1$_m$>K14-wt. The K14-HPV early region fragments were separated from vector sequences by electrophoresis overnight in 4% polyacrylamide gels, electroeluted, and further purified by centrifugation through continuous cesium chloride gradients at 40000 X g for 48 hrs. Fractions (250 μL) were collected from the bottom of each centrifuge tube and samples containing DNA were pooled and then dialyzed against injection buffer, 10 mM Tris/0.1 mM EDTA pH 8.0, for 48 hr at 4° C. The fragment concentrations were adjusted to 2 ng/μl for microinjection.

Transgenic animals were created using standard techniques by microinjecting B6D2/F2 embryos (Hogan, et al., *Manipulating the mouse embryo*, p. 153–173, Cold Spring Harbor Laboratory, Cold Spring Harbor, N.Y. (1986)). The embryos were co-injected with the K14-HPV16 constructs and with K14-β-Galactosidase constructs in a 1:1 ratio. The β-galactosidase constructs were identical to the K14-HPV16 constructs except that the β-galactosidase gene was substituted for the HPV16 early region. Backcrosses to create transgenic lines were predominantly into C57B1/6 and BALB/c animals, and the lineages were maintained as heterozygotes (Table 1).

TABLE 1

Spectrum of pathologies and their penetrance range.

| Type of pathology | No. of Lines* | Penetrance Range (%) Range (%)** |
|---|---|---|
| Ear epidermal hyperplasia/dysplasia | 8 | 100 |
| Facial epidermal hyperplasia/papillomatosis | 6 | 100 |
| Anal papillomas | 5 | 43–82 |
| Truncal ulcers | 2 | 42 |
| Diffuse epidermal hyperplasia | 3 | 45–71 |
| Cataracts | 2 | 25–30 |

*Since there was no correlation between lesional distribution or severity and type of HPV16 transgenic DNA, either wild type or with mutations abolishing the E1 or E2 functions, the results are presented for the entire population of K14–HPV16 mice.
**The number of affected mice/the total number of mice in each line. The phenotypes were analyzed when the mice were from 6–8 months old, although some changes such as ear thickening and acanthosis appeared at a younger age.

Example 2

Transgenic founders and lineages

Three forms of HPV16 DNA were used in this study: wild type, and two or early region variants containing mutations, E1$_m$ and E2$_m$ that abolished the functions of the E1 or E2 genes. Data from keratinocyte transfections comparing these three constructs showed that both mutant early regions were both more efficient than wild type in producing immortalization. Twenty-one founder mice were created, and eight of these founders were bred to generate lineages designated wt #'s 1 and #3, E1$_m$ #'s 1, 4, and 6, and E2$_m$ #'s 1, 5, and 9. The transgenic lines were backcrossed with both C57 and BALB/c mice. During the course of this study 35–60 mice in each line were evaluated.

Example 3

Pathology and penetrance of phenotypes

A spectrum of pathologies arose in the K14-HPV16 transgenic mice, most of which originated in squamous epithelium (Table 1). While there were lineage specific differences in phenotype severity, the differences were not correlated with the type of early region DNA used in the K14-HPV transgenes. These data suggested that expression of the HPV early region behind a strong heterologous promoter was not influenced by E1 or E2 in terms of the severity or the extent of progression of the hyperplastic/dysplastic phenotype.

The epidermis of the ear was consistently affected in all 8 lines, and some degree of hyperplasia arose in every mouse (Table 1). Papillomatosis of the snout and eyelids developed in 6 of the lines with a 100% penetrance (Table 1). Truncal ulcers appeared in areas of pre-existing focal epidermal hyperplasia on the thorax and lower neck in two lines, with a 50% penetrance. Diffuse epidermal hyperplasia occurred in 3 lines (Table 1), and was associated with growth retardation and inability to gain weight despite a greater than normal food intake when normalized for total body weight. Cataracts developed in 3 lines, with a penetrance of approximately 30% (Table 1). These cataracts were the result of circumferential lenticular hyperplasia (data not shown).

Since HPV's are a frequent cause of anal and perineal lesions in humans, it was of interest that anal papillomas developed in 5 lines, with a penetrance ranging from 45–80% (Table 1). These papillomas first appeared between 2–3 months, and all of the affected mice evidenced these lesions by 5 months. The anal papillomas were grape-like, 0.3–0.5 mm masses, circumferentially distributed in the anal squamous mucosa.

Histological analysis of an anal canal from an affected transgenic animal demonstrated a typical papilloma with frond-like epidermal projections, covered by parakeratotic caps and surrounding a central vascularized stalk. A detailed examination of one of the papillary fronds of this lesion revealed cells resembling koilocytes, which are frequently seen in clinical HPV infections.

Example 4

Classification of transgenic lines into phenotype severity groups

The 8 transgenic lines were categorized by the severity of phenotype into groups based on the number of involved epidermal and squamous epithelial sites, and the ultimate degree of ear and facial acanthosis, hyperkeratosis, and papillomatosis (Table 2). Six transgenic lines which were severely affected: E1$_m$ #4, and #6, E2$_m$ #1, #5 and #9, and wt #3. Mice in the severely affected lines developed 4–5 different types of lesions. All of these lines except E2$_m$ #1 displayed extensive acanthotic and hyperkeratotic ear and facial skin changes by 5 months of age. Despite extensive squamous involvement, the average life span of these mice ranged from 8–15 months, which is in contrast to the 2–6 month life span of a line of mice transgenic with a keratin promoted c-Ha-ras that also displays severe epidermal involvement (Bailleul, et al., *Cell* 62:697–708 (1990)). The difference between the wt #1 and the $E1_{nt}$ #1 lines, both of which developed 3 types of lesions (Table 2), was that the an intermediate degree of ear and facial involvement developed in wt #1 line, while both of these phenotypes were barely detectable in the $E1_{nt}$#1 line.

TABLE 2

Classification of transgenic lineages into severity groups based on the number of different types of involved squamous epithelia, and the severity of hyperkeratosis, acanthosis, and papillomatosis of the ears and face, graded 1–4*.

| Severity Group | Transgenic line(s)* | Number and type of involved anatomic site(s) |
|---|---|---|
| Severe | $E1_{tsl}$ #4, 6; | Ear (3-4), face (3-4) |
|  | $E2_{tsl}$ #1 | anus, diffuse epidermal hyperplasia, cataracts |
|  | wt #3, $E2_{tsl}$ #5, 9 | Ear (3-4), face (3-4), anus, diffuse epidermal hyperplasia |
| Moderate | wt #1 | Ear (2), face (2), ulcer |
| Mild | $E1_{tsl\ \#1}$ | Ear (1), ulcer, cataracts |

*Grade 1 changes consisted of mild thickening of the ear skin, and prominence of the conjunctival-epidermal junction, and slight thickness of the snout skin. Grades 2 and 3 included intermediate degrees of ear acathosis and hyperkeratosis, moderate thickening of the conjunctivae junction and mild to moderate papillomatosis of the snout. Grade 4 changes included marked thickening of the ear epidermis, with prominent hyperkeratosis, erythema, and papillomatosis, whereas conjunctival and snout skin changes included erythema and extensive papillomatosis.

**$E1_{tsl}$ has a translation terminal linker at nucleotide 1311, and $E2_{tsl}$ contains a TTL at nucleotide 2922. $E2_{tsl}$ #1 had Grade 1 ear changes, but otherwise was as affected by the remaining phenotypes as $E1_{tsl}$ #4, 6.

Example 5

Progressive histopathological changes leading to dysplasia and papillomatosis

The development of severe ear lesions was progressive in that affected animals had detectable hyperkeratosis by one month of age, which progressed to marked acanthosis, hyperkeratosis, and papillomatosis, by 5 months. Detailed histological analysis was undertaken in one severely affected line, $E1_{nt}$ #4, in order to further characterize these progressive changes. Subsequent biopsies and autopsy material from other lines with similar marked ear involvement confirmed the histopathological analysis from this single line.

The ear of a non-transgenic littermate was composed of 4 layers: columnar basal cells at the dermal/epidermal junction; cuboidal/transverse spinous cells; transverse granular cells; and overlying non-nucleated, eosinophilic cornified cells. The ear of a 1.5 month old transgenic animal contained both mild and moderate epidermal hyperplasia. In areas of mild hyperplasia the basal and granular layers were expanded to two cells in thickness, and the individual keratinocytes were slightly enlarged. While the overall maturation pattern of the epidermis was preserved, there were occasional parakeratotic cells in the stratum corneum, indicative of a focal failure of complete terminal differentiation.

Adjacent microscopic fields demonstrating moderate hyperplastic changes were characterized by a further increase in the thickness of each of the epidermal cell layers, and a greater degree of individual cell enlargement. The ear epidermis from a 5.5 month old transgenic animal contained both hyperplasia and dysplasia. In hyperplastic areas there was marked increase in the size of individual cells, and each of the cell layers was increased three to four fold. The basal cells were spindle shaped and elongated with some nuclear irregularity, while the granular cells contained large, coarse granules. Despite these changes, the maturation pattern of the epidermis was preserved, parakeratosis was still focal, and the stratum corneum was covered with a hyperkeratotic layer several cells thick. An adjacent microscopic field from the same ear displayed atypical basaloid cells with enlarged, hyperchromatic, and irregularly bordered nuclei, which extended into the granular layer, features consistent with a severe dysplasia or carcinoma in situ. These dysplastic areas were also characterized by a decrease in the number of granular cells, and accompanied by a loss of overlying cornification.

In addition, papillomas developed, which were similar in appearance to the anal lesions described above. The focal nature of the histopathology, demonstrating variable degrees of hyperplasia or dysplasia in adjacent fields, was a characteristic feature of the K14-HPV16 transgenic mice, and as such resembles the juxtaposition of normal cervical or anal mucosa to dysplasias observed in patients with HPV16 disease (Crum, et al., *New Engl. J. Med.* 310:880–883 (1984)).

Example 6

Increased and "inappropriate" proliferation in transgenic ear epidermis

A hallmark of neoplastic progression is inappropriate and increased frequency of proliferating cells, which can be identified using S-phase markers or the histological identification of mitotic figures. Histological analysis of transgenic epidermis revealed an increased frequency of mitotic figures, some of which were bizarre. These observations, combined with the progressive hyperplastic changes described in the previous section, suggested that DNA synthesis might be increased in affected transgenic epidermis. In order to examine DNA synthesis, in vivo pulse labeling following a single intraperitoneal injection of BrdU was performed concomitant with histological analysis (see materials and methods). In normal epidermis there were occasional basal and follicular outer root sheath cells in S-phase, and the labeling index in these areas was 6%. In 1.5 month old mildly hyperplastic ear epidermis, the BrdU incorporation was predominantly basal, with only an occasional spinous cell in S-phase, and labeling index was increased to 10%. In 5.5 month old ear skin there was a both an additional increase in the labeling index and a further extension of the abnormal distribution of S-phase keratinocytes. The labeling index in hyperplastic regions ranged from 20–25%, with an increased number of spinous and an occasional granular cell in S-phase. An adjacent microscopic field with pronounced dysplasia demonstrated a further increase in the labeling index to 25–35%, with frequent S-phase cells throughout the granular layer. In normal epidermis terminally differentiated keratinocytes are the sole occupants of the granular layer. Thus the presence of numerous S-phase cells in the granular layer of dysplastic transgenic epidermis suggested that terminal keratinocyte differentiation was profoundly inhibited in these lesions.

Example 7

Abrogation of terminal differentiation in transgenic epidermis

In order to further examine terminal differentiation of the keratinocytes in transgenic epidermis, the expression of specific keratins or envelope associated proteins in adjacent sections of ears was analyzed using immunohistochemistry. Basal keratinocytes exclusively express K14 and K5 (Eckert, *Physiological Rev.* 69:1316–1346 (1989); Kopan, et al., *Genes Dev.* 3:1–15 (1989)). Committed terminal differentiation occurs at the transition between the basal and spinous cells. In spinous keratinocytes, K1 and K10 mRNA and protein are expressed at high levels, whereas K5 and K14 expression is markedly down regulated (Stoler, et al., *J. Cell. Biol.* 107:427–446 (1988)). The expression of K1 and K10 also extends into the granular layer, and in addition these cells express proteins associated with envelope formation such as filaggrin, which macroaggregates the K1/K10 intermediate filaments in preparation for envelope formation, and as such, is a marker for the complete differentiation of the keratinocyte (Eckert, *Physiological Rev.* 69:1316–1346 (1989)). We used specific antibodies directed against several of these molecules in order to precisely characterize the extent and completeness of differentiation in adjacent tissue sections of progressive, $E1_m$ #4 transgenic epidermis described in the previous experiments.

Expression of basal cell specific kentins was investigated using antisera specific for either K5 or K14. The results using either reagent were identical. In non-transgenic epidermis K5 expression was sharply restricted both to the basal layer and the outer root sheath cells of the hair follicle. In mildly hyperplastic, 1.5 month old transgenic epidermis this basal distribution of keratin expression was maintained, but an occasional K5 staining cell was present in the spinous layer. In dysplastic, 5.5 month old transgenic epidermis, there was an overall diminution of K5 staining in the basal layer, along with the striking presence of intensely stained K5 expressing cells in the upper granular layer. Examination of K10 immunostaining revealed minor changes in mildly hyperplastic epidermis, compared to non-transgenic skin. In dysplastic epidermis there was a marked dimuntion in K10 staining throughout the entire suprabasal layers, which was focally undetectable.

The completeness of terminal differentiation was assessed by examining filaggrin expression by the granular keratinocytes. In non-transgenic skin, filaggrin immunostaining was confined to the compressed single layer of subcorneal granular cells. In hyperplastic 1.5 month old transgenic epidermis, filaggrin expression was spread over several layers of suprabasal cells, but was similar to non-transgenic epidermis in its level of expression per keratinocyte. In dysplastic 5.5 month old transgenic skin, there was a striking failure to detect filaggrin over wide areas of the suprabasal layer, with only scattered positive cells detectable. In summary, the persistence of K5 expressing cells in the upper granular layers of dysplastic epidermis suggests that basaloid keratinocytes are inappropriately present in this these layers. The diminution of K10 expression and the near absence of filaggrin indicate that terminal differentiation is abrogated, especially in dysplastic epidermis.

Example 8

Expression of HPV16 E7 RNA and protein in transgenic neonatal skin

HPV transgene expression was first analyzed using RNA-PCR in the skin of K14-HPV16 mice with primers flanking the entire E6ORF (see materials and methods). A specific band consistent with spliced HPV E6* mRNA was present in samples of skin from each of the eight transgenic lines. This fragment is amplified from a combined E6*/E7 transcript, which is the predominant mRNA produced from the HPV16 E6/E7 ORF, and from which the E7 protein is translated (Smotkin, et al., *Proc. Natl. Acad. Sci. USA.* 83:4680–4684 (1986); Smotkin, et al., *J. Virol.* 63:1441–1447 (1989)).

Previously we demonstrated that the HPV16 E7 protein could be detected in tissues of transgenic mice using a combined immunoprecipitation/Western blotting procedure (Arbeit, et al., *Am. J. Path.* 142:1187–1197 (1993)). This technique was used to determine whether HPV16 E7 protein expression was detectable in skin of the K14-HPV16 mice. Full thickness skin pelts, encompassing all of the dorsal and ventral skin between the fore and hind limbs, were obtained from 2 day old neonates. At this age the thickness of the epidermis, determined by microscopy, is equivalent in all of the lines despite the severity of their adult phenotype. E7 protein expression was analyzed from representatives of 6 lines, which varied in adult phenotype severity from mild ($E1_m$ #1), moderate (wt #1), to severely effected (wt #3, $E1_m$#4, and $E1_m$ #6) (Table 2). Immunoprecipitation performed on equivalent amounts of protein extracts from these samples revealed specific 18 kD bands, consistent with the migration of HPV16 E7 protein, present in all of the lines examined. There was no correlation between the amount of detectable neonatal skin E7 protein, and the eventual severity of the adult phenotype. A similar lack of correlation existed between the transgene copy number, determined by Southern blotting, and ultimate phenotype severity. In situ hybridization analysis of transgenic ear epidermis suggests that focal upregulation of K14-HPV16 expression occurs during progression and correlates with the extent of pathology. Thus, while the distribution and ultimate severity of the adult phenotype cannot be predicted from the level of neonatal transgene expression, focal upregulation of the HPV early region in individual keratinocytes may be the key determinant of phenotype severity.

Example 14

K14-HPV16 transgenic mice- A model of multistep epidermal neoplastic progression The changes in histopathology, BrdU incorporation, and keratin/filaggrin immunohistochemistry during ear epidermal progression in markedly affected transgenic mice are summarized in Table 3. Similar to HPV16 disease in humans, there is focal variation in these changes, with adjacent microscopic fields displaying different appearances and biochemical abnormalities. This focal variance prevents a strict correlation of one type of lesion (i.e., mild hyperplasia vs. hyperplasia vs. dysplasia) with increasing age. Rather what is correlated with increasing age is the frequency and extent of a particular lesion. In 3–6 week old mice, mild and established hyperplasia are present in approximately equal frequency. Mild epidermal hyperplasia has a BrdU labeling index ranging from 10–15%, and a keratin/filaggrin immunohistochemistry profile that is similar to a non-transgenic ear, but with changes consistent with an increase of the basal cell layer to twice that of normal skin (Table 3). By two months of age there is an almost uniform distribution of hyperplasia, with rare loci of dysplasia. The labeling index of hyperplasia ranges from 20–25%, and the keratin/filaggrin immunohistochemistry profile is similar to that of mild hyperplasia, with more pronounced changes consistent with a two -three fold expansion of all of the epidermal cell layers (Table 3).

By 3–5 months of age there is a marked increase in the frequency of dysplasia. The BrdU labeling index of dysplastic lesions ranges from 25–35%, with numerous S-phase keratinocytes in the upper granular layer. The keratin/filaggrin immunohistochemistry profile is markedly abnormal with K5/K14 expressing keratinocytes present in the upper granular layer, and marked diminution in suprabasal K10 and filaggrin expression (Table 3). These changes in keratin immunohistochemistry are consistent with a profound abrogation of epidermal keratinocyte differentiation in dysplastic ear lesions.

toxicity, and a specific urinary obstruction from this dose when treatment is extended longer than 2 months. Thus the lower 0.25 mg dose may well be better for prolonged experiments lasting 4–8 months of treatment. There is encouraging data, in a large number of animals, which suggests that this dose indeed induces the same changes in the cervico-vaginal mucosa as the higher dose. Further, several drug companies are using a similar low dose of estrogen to treat mice for prolonged periods. In long term

TABLE 3

Characteristics of the stages of epidermal neoplastic progression in K14-HPV transgenic mice.

| Stage | Histology | Labeling Index (%)* | Expression of: | | |
|---|---|---|---|---|---|
| | | | KS/14** | K10 | Filaggrin |
| Normal | 4-layer epidermis | 6 | Restricted to basal layer | Suprabasal layer | Granular layer |
| Mild hyperplasia | Basal layer increased 2X | 10–15 | Present in basal/spinous layer | Suprabasal layer | Granular layer |
| Hyperplasia | All layers increased in thickness, differentiation normal | 20–25 | Extends to lower granular layer | Decreased in suprabasal layer | Present in mulitple granular layers |
| Dysplasia | Basaloid cells in granular layer | 25–35 | Detectable in upper granular layer | Further decreased in suprabasal layer | Barely detectable in in granular layer |

*The labeling index was determined by the incorporation of BrdU following a 2 hr pulse administered intraperitoneally.
**The expression of keratin and filaggrin was assessed by immunohistochemistry.

Example 10

Effect of Exogenous Estrogen

The treatment of the K14-HPV16 transgenic mice with exogenous estrogen turns on transgene expression in the squamous mucosal basal cells of both the vagina and the cervix. Further of greater clinical and therapeutic relevance, is that estrogen induced HPV16 transgene expression produces neoplastic progression that faithfully resembles the gynecological dysplastic lesions induced by high risk HPV'S. The specific protocol followed is described herein.

Virgin K14-HPV16 females were treated at 4–6 weeks of age. Commercially available estrogen pellets containing either 0.72 or 0.25 mg 17-β-estradiol were implanted subcutaneously. These pellets release this estrogen dose over 60 days. Mice were treated with estrogen for periods ranging from 1–4 months, by re-implanting additional pellets for treatments beyond 60 days. One month of estrogen treatment produces sporadic dysplastic keratinocytes in the cervix and vagina. Thereafter for periods ranging from 2–4 months, the frequency of dysplastic cells and the overall grade of dysplasia incrementally increased. Control non-transgenic mice treated with the same dose of estrogen for similar treatment periods developed a thickening of the cervico-vaginal mucosa which was due to an increase in the number of cervico-vaginal keratinocytes, but these keratinocytes are normal in appearance without dysplastic changes. Thus, in this transgenic mouse model, estrogen treatment conditionally and selectively upregulates the expression of HPV16 not only in the clinically relevant target tissue; the gynecological squamous epithelium, but also within the critical cells, the basal keratinocytes, within this epithelium. Estrogen treatment is therefore able to induce the precise pathology, cervico-vaginal squamous dysplasia that is caused by HPV16 disease in humans.

The data detailing the development of cervico-vaginal dysplasia has been obtained with the 0.72 mg pellets, however the mice appear to develop a generalized low level experiments these pellets will be re-implanted every 60 or 90 days (a longer duration 90 day release form of the pellet is also available). Regardless of the eventual dose of estrogen, these transgenic mice are potentially a powerful model of gynecological neoplastic progression.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A transgenic mouse, wherein the genome of the mouse has integrated into it an HPV early region oncogene operably linked to a promoter, wherein the promoter regulates expression of the oncogene in a transient amplifying cell, and where expression of the oncogene results in the mouse developing progressive epidermal neoplasia.

2. The mouse of claim 1, wherein the transient amplifying cell is a basal keratinocyte.

3. The mouse of claim 1, wherein the oncogene is HPV-16 E6 or E7, or both HPV-16 E6 and E7.

4. The mouse of claim 1, wherein the promoter is the keratin-14 promoter.

5. The method of claim 1, wherein the epithelial neoplasia is in epidermal tissue of the mouse.

6. The mouse of claim 1, further comprising a β-galactosidase gene operably linked to a promoter which regulates expression of the β-galactosidase gene in a transient amplifying cell.

7. The mouse of claim 6 wherein the transient amplifying cell is a basal keratinocyte.

8. The mouse of claim 6, wherein the promoter is the keratin-14 promoter.

9. A method for determining the efficacy of a composition to inhibit progressive epithelial neoplasia, the method comprising, providing a transgenic mouse, wherein the genome of the mouse has integrated into it an HPV early region oncogene operably linked to a promoter, wherein the promoter regulates expression of the oncogene in a transient amplifying cell, administering the test compound to the mouse; and monitoring the mouse for progressive epithelial neoplasia.

10. The method of claim 9, wherein the neoplasia is in epidermal tissue of the mouse.

11. The method of claim 9, wherein the oncogene is HPV-16 E6 or E7, or both HPV-16 E6 and E7.

12. The method of claim 9, wherein the mouse further comprises a β-galactosidase gene operably linked to a keratin-14 promoter.

* * * * *